(12) United States Patent
Weisberg

(10) Patent No.: US 9,279,796 B1
(45) Date of Patent: Mar. 8, 2016

(54) LASER EYE-SAFETY METHOD AND APPARATUS

(71) Applicant: Arel Weisberg, East Brunswick, NJ (US)

(72) Inventor: Arel Weisberg, East Brunswick, NJ (US)

(73) Assignee: Energy Research Company, Plainfield, NJ (US)

( * ) Notice: Subject to any disclaimer, the term of this patent is extended or adjusted under 35 U.S.C. 154(b) by 0 days.

(21) Appl. No.: 14/277,302

(22) Filed: May 14, 2014

Related U.S. Application Data

(62) Division of application No. 13/459,956, filed on Apr. 30, 2012.

(60) Provisional application No. 61/518,118, filed on Apr. 29, 2011.

(51) Int. Cl.
*G01N 33/22* (2006.01)

(52) U.S. Cl.
CPC .............. *G01N 33/22* (2013.01); *G01N 33/227* (2013.01)

(58) Field of Classification Search
CPC ............................ G01N 33/227; G01N 33/22
See application file for complete search history.

(56) References Cited

U.S. PATENT DOCUMENTS

| | | | |
|---|---|---|---|
| 6,608,677 B1 * | 8/2003 | Ray et al. | 356/301 |
| 8,085,410 B1 * | 12/2011 | Hargabus | 356/614 |
| 2004/0198336 A1 * | 10/2004 | Jancic et al. | 455/420 |
| 2009/0219961 A1 * | 9/2009 | Meyers et al. | 372/29.01 |
| 2011/0040358 A1 * | 2/2011 | Bean et al. | 607/89 |

* cited by examiner

*Primary Examiner* — David Porta
*Assistant Examiner* — Mindy Vu
(74) *Attorney, Agent, or Firm* — Ronald B. Goldstein

(57) ABSTRACT

A method and apparatus are described for detecting the presence of explosives. The invention utilizes Laser Induced Acoustics (LIA), wherein an area of a substrate surface is irradiated, via deep UV pulsed laser, with laser pulses to generate a detectable audible signal. The invention also provides substantial improvements in the eye-safety of otherwise potentially harmful laser beams. Thus, the invention is particularly well-suited to use in public venues where detection of explosives or improved laser safety may be required.

6 Claims, 13 Drawing Sheets

LASER EYE-SAFETY METHOD AND APPARATUS

CROSS-REFERENCE TO RELATED APPLICATIONS

This application claims priority to U.S. Provisional Application No. 61/518,118, filed Apr. 29, 2011, and is a divisional of U.S. Ser. No. 13/459,956, filed Apr. 30, 2012.

BACKGROUND OF THE INVENTION

1. Field of the Invention

The invention relates to the detection of explosives in public locations and, more particularly, to a method and apparatus for detecting trace amounts of explosives on various surfaces.

Increasingly, public safety and the safety of government and military personnel depends on the detection of hidden explosives in venues such as airports and other transportation terminals, subway entrances, border crossings, sporting events, concerts, and other public gatherings. The presence of an explosive film or explosive particles on a surface is a possible indicator that larger amounts of explosives are nearby. For example, an explosive-laden fingerprint on a car's trunk lid, as may be detected by the present invention, may be an indicator that a large amount of explosives is inside the trunk.

The invention also relates to improvements in the eye-safety of laser emissions, so as to meet U.S. regulatory standards. Such improvements will allow for greater public use of laser-based instruments and techniques including, but not limited to, those disclosed herein for the detection of explosives.

2. Description of the Related Art

It is desirable to be able to detect explosives from a "safe distance." A number of methods for such "stand-off" detection of explosives have been disclosed in the art, including certain methods utilizing lasers.

One laser-based method known in the art involves the use of Raman Spectroscopy, wherein a laser shining on a material excites molecular vibrations in the irradiated molecules. This results in emission of an optical spectrum that is unique to the chemical compounds present in the material. Variations on this method include Coherent Anti-Stokes Raman Spectroscopy (CARS), Surface Enhanced Raman Scattering (SERS), and Resonance Raman Spectroscopy.

Another method, known as Laser Induced Breakdown Spectroscopy (LIBS), uses a laser to ablate a small amount of a material and excite the ablated mass into a high-temperature plasma. The optical spectrum of the plasma then is used to identify the elemental composition of the ablated mass.

In Photodissociation/Laser Induced Fluorescence, laser light is used to photodissociate any unstable molecules on a surface and subsequently cause the dissociated molecular fragments to fluoresce. The fluorescence spectrum is then analyzed for the presence of telltale markers for fragments of explosive compounds.

A suite of related methods, collectively known as Laser Absorption Spectroscopy, is based on the absorption of laser light at different wavelengths as a laser beam passes through air above a surface containing explosives or explosive residues. Vapor from the explosive compounds absorbs the laser light at characteristic wavelengths that are unique to those compounds. This approach is also known by the acronym "LIDAR" (light detection and ranging), which is a general term often used to describe any kind of stand-off, laser-based vapor detection.

The phenomenon of laser absorption can also be used to detect the solid phase of explosive compounds. This technology exploits the fact that the reflectivity of a surface changes when a trace amount of explosive compound is present on it. The reflectivity is measured, usually in the mid-infrared region of the spectrum, over a range of wavelengths by using a tunable laser, most commonly a quantum cascade laser. As the laser wavelength changes, the magnitude of the reflected light is measured. The resulting spectrum of reflected light reflects the chemical makeup of the compound on the surface. Comparing the collected spectrum to a library of reflectance spectra collected from different explosives allows for identifying trace amounts of unknown compounds. See, e.g., U.S. Pat. Nos. 7,894,057 and 7,368,292.

The patent literature is replete with such methods of detection. For example, U.S. Pat. No. 5,420,905 discloses a method using resonance fluorescence and resonance absorption (preferably utilizing bremsstrahlung or other continuous-spectrum photon radiation) to detect explosives in a target such as a piece of luggage or other container. The utility of this method generally is limited to detecting explosives characterized by high concentrations of both nitrogen and oxygen, but also having a low concentration of carbon. The method utilizes a detecting apparatus to capture, measure, count, and record the energies of photons scattered from the target. This detecting apparatus requires appropriate filtering and shielding.

U.S. Pat. No. 5,818,047 discloses a method utilizing Raman Spectroscopy to detect Semtex plastic explosive, the active ingredients of which are RDX (cyclotrimethylene-trinitramine) and PETN (pentaerythritol-tetranitrate), in a sample such as a fingerprint on an aircraft boarding card.

U.S. Pat. No. 6,104,190 discloses a method and apparatus for detecting the presence of a nitramine explosive (such as RDX), wherein a radio frequency (RF) signal is emitted towards a target. If the target contains a chemical compound having a nitro group, excitation of such compound will produce a detectable Nuclear Quadrupole Resonance (NQR) signal.

U.S. Pat. No. 6,295,860 discloses an explosive detection system in which vapor leaking from luggage is sampled by a sampling probe; negative corona discharge is used to ionize the vapor; and a mass spectrometer is used to detect the ionized vapor, thereby determining whether or not an explosive is present.

U.S. Pat. No. 6,477,907 discloses an apparatus and method for detecting explosive-indicating compounds in subsurface soil. The apparatus has a probe with an adsorbent material on its surface and can be placed into soil beneath the ground surface, where the adsorbent material can adsorb explosive-indicating compounds. The explosive-indicating compounds are then desorbed and transferred as either a liquid or gas sample to a diagnostic tool (such as an ion-mobility spectrometer, a gas chromatograph, a high performance liquid chromatograph, a capillary electrophoresis chromatograph, a mass spectrometer, a Fourier-transform infrared spectrometer or a Raman spectrometer) for analysis.

U.S. Pat. No. 6,828,795 discloses an explosive detection system utilizing an ion mobility spectrometry instrument to detect the presence of trace molecules in air. A directed emission of photons, typically in the form of infrared or visible light, warms a target object, so as to significantly enhance vapor emission therefrom, which improves the sampling efficiency. A cyclone sampling nozzle also improves the sampling efficiency, particularly when the sampling needs to be performed at a distance from the air intake.

U.S. Pat. No. 6,928,131 discloses a method, utilizing X-rays, to detect an explosive in an object, such as inside a piece of luggage or mail. X-ray images of the object are used to detect areas containing a high density of organic materials and/or unidentified articles therein. Any such areas then are further characterized with respect to location, dimensions and supposed mass of any unidentified article therein. The method further includes thermal neutron irradiation of the area containing any such unidentified article; recording the output using gamma-ray detectors; determining a threshold value for the overall gamma-ray intensity based on the supposed mass of explosive being detected; and determining the presence of an explosive in the event the threshold value of overall gamma-ray intensity is exceeded. When checking small-size objects with this method, the neutron irradiation step is preceded by replacing the ambient air by a gaseous medium not containing nitrogen.

U.S. Pat. No. 6,967,103 discloses an explosives detector utilizing an array of molecularly imprinted polymer (MIP) coated, bifurcated fiber optic cables to form an image of a target molecule source. Individual sensor fiber assemblies, each with a calibrated airflow, are used to expose the fibers to the target molecule. The detector energizes a dedicated excitation light source for each fiber, while simultaneously reading and processing the intensity of the resulting fluorescence that is indicative of the concentration of the target molecule. Processing electronics precisely controls the excitation current, and measures the detected signal from a plurality of narrow band pass filters and photodiodes. A computer then processes the data to form and display an image of the target molecule source.

Finally, U.S. Pat. No. 7,239,974 discloses a method for monitoring thermal emissivity levels of human traffic in public venues. The method uses an infrared detector such as a quantum well infrared photodetector (QWIP) equipped camera. Based on differential emissivity calculations, a determination is made whether the monitored emissivity level corresponds to at least one calibrated emissivity level associated with an explosive material. The monitored emissivity levels are calibrated to eliminate the effects of other synthetic objects such as clothing, personal items, and other harmless objects. The monitored emissivity levels also are buffered against changes in environmental factors.

The above-described methods have multiple disadvantages. Typically, such methods involve optical emissions. Detection and analysis of these emissions may require very expensive equipment (e.g., a spectrometer). Moreover, such optical emissions may not be unique to explosives or may be difficult to discern from emissions caused by (a) the particular substrate on which an explosive film is deposited or (b) other compounds also deposited on the substrate (e.g., dirt, grease). Such methods also may require the use of multiple lasers, adding to the cost and complexity of the respective systems. Significantly, the efficacy of the above methods may be limited to detection of nitrogen-based explosives, so that other types of explosives are not identified. Finally, many of these methods are not sufficiently rapid, requiring many seconds or minutes to complete an analysis. Thus, when such prior art methods are used to test luggage or other personal items for explosives, unacceptable delays may arise, especially under circumstances where the respective owners of the luggage or other personal items are required to wait during the test.

Thus, it would be desirable to be able to provide a quicker, more accurate, and less expensive means of detecting a greater variety of explosives, especially in areas having a high volume of human traffic.

SUMMARY OF THE INVENTION

The above-identified shortcomings of the prior art are remedied by the present invention, which utilizes a novel methodology described herein as Laser Induced Acoustics ("LIA"). The invention provides a method and apparatus for generating and analyzing acoustic emissions from explosives, particularly those present as a film or as small particles, whether the film and particles are visible to the naked eye or not, on the surface of an object, in order to rapidly and reliably discern the presence of such explosives. The method may be used in the types of public, government, and military venues described above. The invention also may be used, for example, in a forensic role by investigators trying to determine whether explosives were once present at a crime scene.

The invention is based on the discovery that even trace amounts of explosive compounds on various substrates produce a distinct "snapping" sound when irradiated with a low energy ultraviolet ("UV") laser that emits pulses several nanoseconds long. It should be noted that a similar snapping sound typically can be made to occur when a UV laser irradiates a substrate that is completely free of explosive. However, characteristics of the snapping sound are different when trace amounts of an explosive are present as compared to when the substrate is free of explosive. Additionally, when certain types of explosives are present, the snapping sound occurs at lower laser pulse energies than would be required where the substrate is free of explosive.

The invention further provides a method and apparatus to render the laser pulses "eye-safe" according to U.S. regulatory standards, thereby making the invention especially amenable to public uses. This is a significant advantage over other laser-based methods for explosives detection, whose ultimate utility is limited by the dangerous laser pulses they emit (both their direct laser pulses, as well as the reflections of such laser pulses). In the first instance, since ordinary glass is essentially opaque to the very short wavelength of the laser used in the practice of the present invention, glass shields may be deployed effectively and inexpensively. Moreover, the inventive method utilizes ancillary laser beams as optical "trip wires" to ensure that no person enters the beam path. Finally, a visible laser beam, such as that from a laser pointer, is overlaid on the UV laser pulses. Because any person whose eyes are in the path of the UV laser pulses or their reflections would see the visible light from the laser pointer and turn away rapidly (in 0.25 seconds according to the U.S. federal standard), the person's exposure to the UV laser pulses is limited to levels below the federal standard.

Thus, in a first embodiment of the invention, a method and a corresponding apparatus are provided for detecting the presence of an explosive compound on a surface of interest. The invention includes:

irradiating an area of said surface with ultraviolet laser pulses; and measuring (e.g., with a microphone or other audio sensor or detection device) an acoustic signal produced by said irradiated surface.

In an additional embodiment, the invention further includes determining a threshold laser energy level at which the same type of surface, if free of explosive, would generate an acoustic signal.

In a further embodiment, the invention includes comparing the threshold laser energy level determined for the explosive-free surface with the actual laser energy level at which the surface of interest produces an acoustic signal.

In another embodiment, the invention includes comparing (i) the amplitude during the duration of the acoustic signal generated by the irradiated surface of interest with (ii) the amplitude during the duration of the acoustic signal that would be generated by the same type of surface, if free of explosive.

In another embodiment, the invention includes comparing (i) the amplitude during the duration of the acoustic signal generated by the irradiated surface of interest with (ii) the amplitudes during the durations of signals stored in a library of stored signals from different explosives for the purpose of identifying the type of explosive present on the surface.

As an alternative to comparing the amplitudes of the respective acoustic signals, such signals instead may be compared based on other qualities of the signal, e.g., by first converting the signals, via a Fourier Transform, for a frequency or spectrum analysis.

In another embodiment, the invention includes using mathematical algorithms that compare a collected acoustic signal, or a portion thereof, to a library of collected acoustic signals from different explosives and, optionally, non-explosive materials, to determine if an explosive residue ("residue" should be taken to mean the aforementioned film or particles of explosive material) is present. Also optionally, these algorithms can also be used to determine the type of explosive if such a residue is found. These algorithms are often commonly referred to as "chemometric" methods. More generally, these belong to the larger mathematical family of statistics and statistical analysis, artificial intelligence, and machine learning algorithms.

In another embodiment of the invention, the laser and the microphone (or other audio sensor or detection device) are not located close to one another and, preferably, the microphone is placed closer than the laser to the surface of interest. The benefit of this is to be able to use lower, and hence safer, laser pulse energies. When the laser is placed far from the surface of interest and low laser pulse energy levels are applied, the resulting sound amplitude may be too low to be detected by a microphone that is placed at the same distance as the laser from the target surface. By placing the microphone nearer than the laser to the target surface, for example, by placing it on a remote-controlled vehicle that is directed to a location close to the target surface, a lower (and thus safer) laser pulse energy may be used, without compromising the microphone's ability to detect relevant audible signals. This has the additional benefit of keeping the generally expensive laser a safe distance from the target surface and only risking the relatively inexpensive microphone in the more hazardous area near the target surface.

In yet a further embodiment, the invention additionally includes determining the molecular characteristics of said surface via Laser Induced Breakdown Spectroscopy and/or Raman Spectroscopy.

Another aspect of the invention provides a method and corresponding apparatus for improving the eye-safety of potentially harmful laser pulses. This aspect of the invention includes:

positioning one or more ancillary lasers, so that an ancillary laser beam or stream of laser pulses is proximate to, but at least partially outside, the area irradiated by the primary laser pulses; and in the event of any discontinuity in an ancillary laser beam or stream of laser pulses, generating a signal to shut off the primary laser. The ancillary laser beams or stream of laser pulses are of a type considered to be less potentially harmful than the primary laser beam.

Additional embodiments of the invention that provide improved eye-safety include (a) limiting the range to target over which the primary laser will fire and/or (b) disposing a visible laser beam so as to be substantially coincident with said primary laser beam.

DETAILED DESCRIPTION OF THE INVENTION

Figure 1:
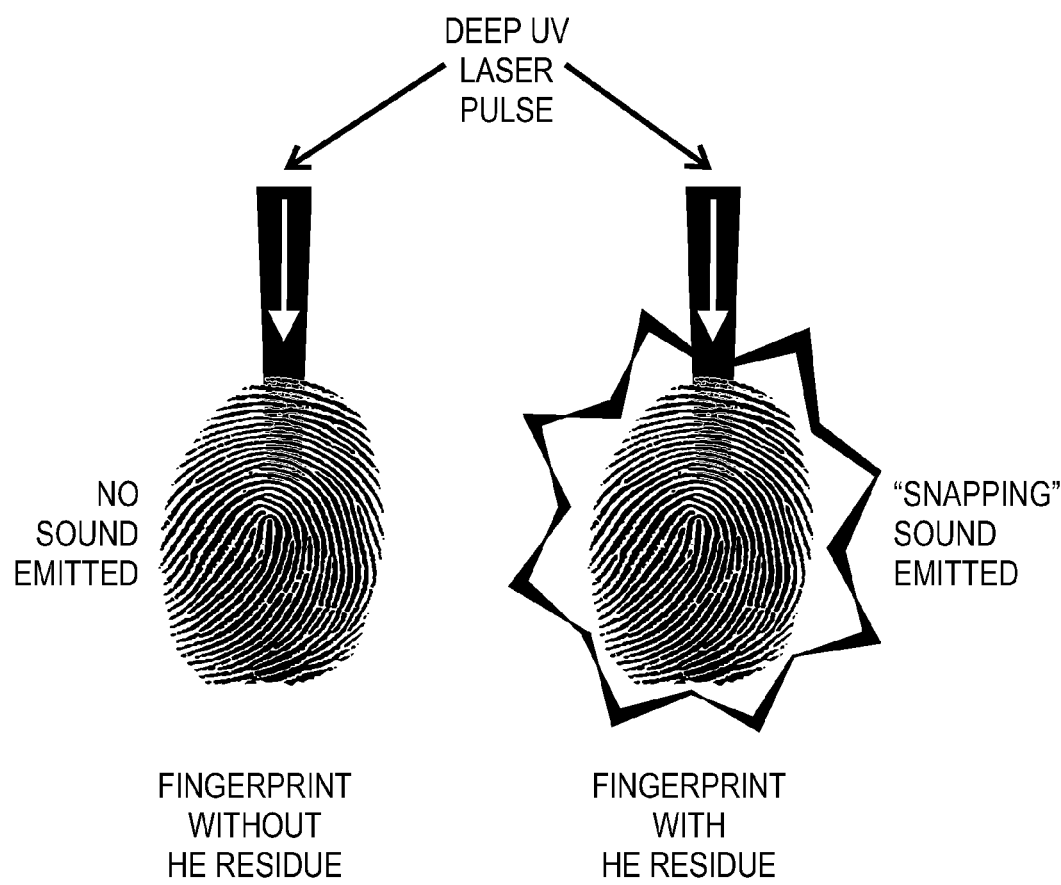
FIG. 1 is a conceptual illustration of the detection of explosives ("HE"=high explosives) in a human fingerprint in accordance with the invention.

LIA (Laser Induced Acoustics), as provided by the present invention, is a novel approach to detecting the presence of explosives. LIA utilizes a deep UV pulsed laser and a microphone attached to a high-speed data acquisition (DAQ) system. As used herein, the term "microphone" shall be understood to include any traditional microphone or acoustic transducer, as well as other audio sensors or detection devices or methods, such as Laser Doppler Vibrometry as described in Example 7 below. The laser operates preferably at a wavelength from about 193 nm to about 280 nm, and more preferably at a wavelength from about 213 nm to about 266 nm.

The inventive method involves irradiating a spot on a substrate surface with laser pulses to generate a detectable audible signal, characterized by a very weak snapping sound. Such audible signal typically is detectable from a distance of at least 10 meters, even with considerable ambient noise and non-ideal detection equipment. While the signal typically is detectable from 10 meters away, this does not imply LIA is only useful for this distance. A LIA system can be engineered to detect to explosives from as close as being in contact or nearly in contact with the surface being scanned, and it can be engineered to operate from standoff distances of 100 meters or more.

Preferably the LIA device is placed at a safe distance from the substrate of interest. In this context, a "safe distance" means far enough away from the substrate so that the LIA device, or at least any human operator of the equipment, would not be harmed in the event of an explosion or harmed considerably less than if a method of testing were used that required the operator to come into close contact with the substrate. Examples of close contact methods include x-ray analysis, ultrasound analysis, and swiping a surface and then analyzing any residue on the swipe, often by ion mobility spectroscopy (IMS).

Placing the microphone closer to the target surface can be accomplished by a number of different methods. The military uses small robots for explosive ordnance disposal activities. Popular models of these robots are the iRobot Packbot (http://www.irobot.com/en/us/robots/defense/packbot.aspx) and the QinetiQ Talon (http://www.qinetiq.com/what/products/Documents/Talon-Robotics-Brochure-QinetiQ.pdf). Placing the and LIA system or just the microphone of a LIA system on these types of robots would increase their capabilities in detecting explosives. These robots are remote controlled. However, the military is also developing autonomous robot vehicles that similarly could serve to bring a LIA system or a LIA system's microphone close to a target. More advanced technologies can also serve this role. Researchers at the Massachusetts Institute of Technology have developed autonomous flying robots capable of hovering near a target (http://web.mit.edu/newsoffice/2006/flyingrobots.html). Flying robots such as these could carry a LIA system's microphone close to the target surface.

LIA detection is especially advantageous in that it can be based on changes in a surface's reactivity to laser radiation, regardless of the actual composition of the surface. There are two ways to take advantage of this. In the first method, LIA signals for a particular substrate are first measured on a part of the surface where explosive residue is not suspected, and then LIA signals are measured again where explosive residue is suspected. Since adding an explosive residue to a material makes such material react differently to laser energy, it is expected that the LIA signal from any surface will demonstrably change with the addition of an explosive residue. Thus, the base-line reactivity of a particular surface material is not of consequence, because the only consequential measurement is of the change in the LIA signal due to the presence of explosive on such surface.

Since identifying and testing an area on the target surface that is known to be free of explosive residue isn't always practical, (for example, in the case of a car door handle), a second method may be necessary to take advantage of the change in a surface's reactivity to LIA laser pulses when an explosive compound is present. There is an expectation that the explosive residue is not distributed uniformly, but rather in particles or small pockets of film that are randomly distributed on the surface. In this case, when LIA signals are collected from the entire area of interest (e.g., a car door handle) some of the signals will arise from the explosive particles or film, some will arise from clean substrate, and some will arise from spots where the laser pulses struck both explosive and substrate. The second method for taking advantage of changes in a surface's reactivity to LIA laser pulses is to use mathematical algorithms to divide the measured signals into categories corresponding to the explosive/substrate/mixture categories. Algorithms that perform automatic grouping of signals are known to those of skill in the art as unsupervised classification algorithms, unsupervised pattern recognition algorithms, and clustering algorithms. A common algorithm of this type is known as the K-means algorithm, which has been applied to acoustic signals in the literature (for example, Azarbarzin, A. and Moussavi, Z., "Unsupervised classification of respiratory sound signal into snore/no-snore classes", Engineering in Medicine and Biology Society (EMBC), 2010 Annual International Conference of the IEEE, 2010, pp. 3666-3669). Other methods include hidden Markov models and Gaussian mixture models (for example, Adi, K., Johnson. M. T., Osiejuk, T. S., "Acoustic censusing using automatic vocalization classification and identity recognition", J Acoust Soc Am. 2010 February; 127(2):874-83.)

Alternatively, libraries of LIA signals from different surfaces and different substances can be generated under controlled conditions, such as in a laboratory, and stored on a computer. Then, newly collected LIA signals can be compared to those in the library to determine if the applicable signal is from an explosive compound.

The present invention is useful in the detection of either nitrogenous or non-nitrogenous explosives. Typical explosives, amenable to detection using the present invention include, but are not limited to, Commercial explosives such as Detasheet, nitroglycerin, EGDN, black powder, and smokeless powder;
Military explosives such as TNT, RDX, PETN, and HMX;
Blends of explosive compounds with binding or plasticizing agents, such as C4, Semtex, Composition B, and dynamite;
"Homemade" explosives such as ammonium nitrate, ammonium nitrate fuel oil (ANFO), urea nitrate, and TATP;
Chlorate explosives such as potassium perchlorate, sodium perchlorate, and ammonium perchlorate.

In a preferred embodiment of the invention, the laser pulse energy is selected so as to be able to generate a LIA signal for a clean substrate. The laser pulses are scanned across the substrate and the resulting LIA signals are recorded. Each signal is compared to a library of signals from different explosive compounds to see if any match closely. Preferably this comparison is done using chemometric methods as described above and below. If a close match is found, the system reports that an explosive compound has been detected. In a preferred embodiment, the system then reports the closest or the few closest matches in the library so the operator knows which type of explosive was found or suspected to be found. Optionally, a library of signals from clean substrate materials and common non-explosive compounds can also be included in the system's library of LIA signals as a means of reducing false alarms.

The chemometric methods described above need to be trained with the electronic library of LIA signals to be able to detect explosives when deployed. This training involves labeling each library LIA signal as belonging to a certain class of explosives or non-explosive materials. Different embodiments of the invention can have different classification schemes. One embodiment involves assigning each type of material its own class. For example, the explosive TNT would be considered to be in a separate class from the explosive PETN. Another embodiment involves grouping together explosives that share a commonality. For example, TNT and PETN would be members of a class of nitrogenous explosives, while the explosive TATP would be a member of a different class—the class of peroxide based explosives. As a further example, the various explosives would be classified according to whether these are commercial/military explosives or "homemade" explosives.

In an alternate embodiment, all explosives would be grouped into one class. The benefit of having fewer classes is that the probability of a false alarm (i.e., determining that an inert surface has an explosive compound on it when, in fact, it does not) increases when a greater number of classes must be tested. By contrast, the benefit of using more classes is that the training is more individualized, so the likelihood of detecting an explosive compound when one is present is increased, as is the likelihood of identifying the explosive correctly. Certain operational scenarios will favor increased detection rates and will be able to tolerate the increased false alarm rate, while other scenarios will be able to tolerate a lower detection rate with the benefit of fewer false alarms. Therefore, the invention advantageously provides a number of different embodiments with respect to training the chemometric algorithms.

When scanning a surface for trace amounts of explosive with LIA, many LIA signals will be collected, some of which may be identified by the LIA system as coming from an explosive compound. In one embodiment of the invention, a mathematical algorithm is used to determine whether to alert the user that trace amounts of an explosive have been found. The reason why an algorithm is needed for this task is that false alarms are inevitable. The mathematical algorithm will examine the number and spatial pattern of LIA signals that were determined to be due to the presence of an explosive. If the number and/or pattern are suggestive of, for example, a fingerprint, then the confidence in the finding is boosted. On the other hand, if only a small number of LIA signals were determined to be due to the presence of an explosive, and these signals were randomly and widely distributed over the scan area, this would increase the probability that the result was due to a false alarm. Mathematical algorithms that perform this type of analysis fall under the general categories of expert systems, fuzzy logic, and artificial intelligence.

In one embodiment of the invention, the LIA signals for the electronic library of signals are collected in a noise-free environment, such as an anechoic chamber. Because LIA is an acoustic technology, LIA signals are subject to interference from ambient noises whose characteristics are unique to that location and time. Therefore, collecting LIA signals for the electronic library in the noise-free environment of an anechoic chamber will result in an electronic library of LIA signals uncontaminated by noise. This will ensure that when a LIA signal collected in the field is compared to the library of signals, the closeness of a match is based on the essential features of the explosive's LIA signal and not on an extraneous feature introduced by noise.

In another embodiment, an explosive is detected by exploiting the property of certain explosive compounds to reduce the necessary laser pulse energy to generate a LIA signal. In this embodiment, the laser energy is set above the LIA threshold for high sensitivity explosives, but below the LIA threshold for the applicable substrate. In such a case, only an explosive-contaminated substrate will produce an audible signal upon irradiation with the laser; an explosive-free substrate will produce no such signal. FIG. 1 provides a conceptual illustration of how such an approach may be used to detect the presence of a trace amount of explosives ("HE"=high explosives) in a human fingerprint. This embodiment will be used in the experimental Examples 1 to 3 below, to demonstrate how LIA detects explosives. A preferred embodiment is described in experimental Examples 4 and 5 below.

An especially preferred embodiment of the invention comprises a single sensor apparatus in which LIA is combined with LIBS and/or Raman Spectroscopy capabilities. As described above, Raman Spectroscopy identifies molecules with a laser, and LIBS measures elemental composition. While not wishing to be bound by theory, it is believed that LIA operates via some kind of photo-dissociation effect. The benefit of combining two or three such independent methods (i.e., LIA, with LIBS and/or Raman Spectroscopy) into a single sensor apparatus is that both false positive readings and false negative readings should be reduced. Moreover, the benefit of adding LIA to a LIBS/Raman Spectroscopy sensor would be substantial while the added cost would be modest, since most of the cost is for the laser, which is already present for the Raman and/or LIBS measurements. The addition of a microphone, amplifier, and DAQ system, as described above, may add no more than about $1000 in hardware costs.

EXPERIMENTAL EXAMPLES

Figure 2:
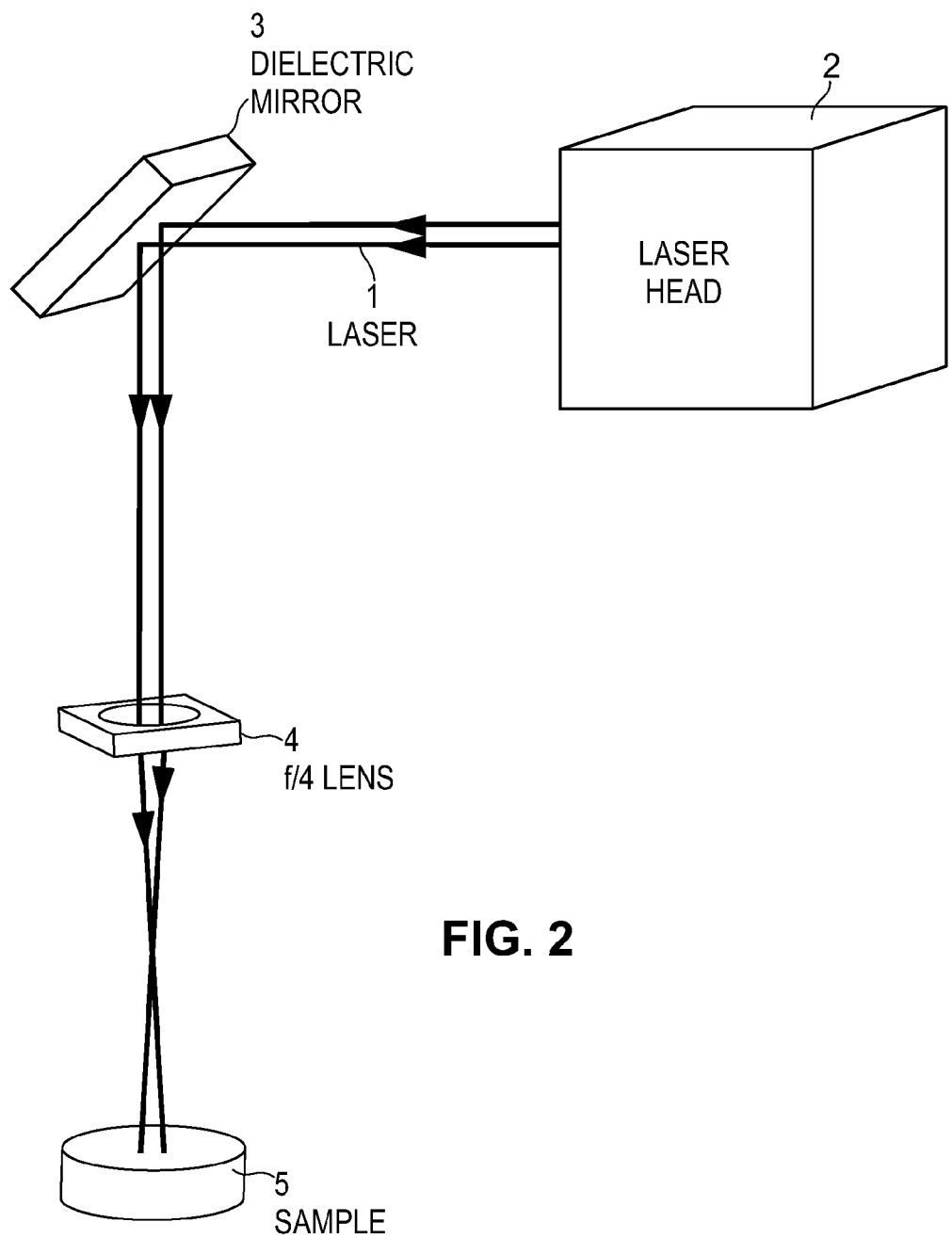
FIG. 2 depicts a typical "bench setup" for LIA measurements as performed in accordance with the experimental Examples set forth herein.

The experimental setup for the LIA measurements described in the Examples below is as shown in FIG. 2 and FIG. 3. As can be seen in FIG. 2, pulses of ultraviolet light 1 from Laser Head 2 were reflected off a 45-degree dielectric mirror 3 and directed through an f/4 lens 4 onto a sample/target surface 5. The lens was placed such that the laser light was diverging to a diameter of 3.5 mm as it intersected the target.

Figure 3A:
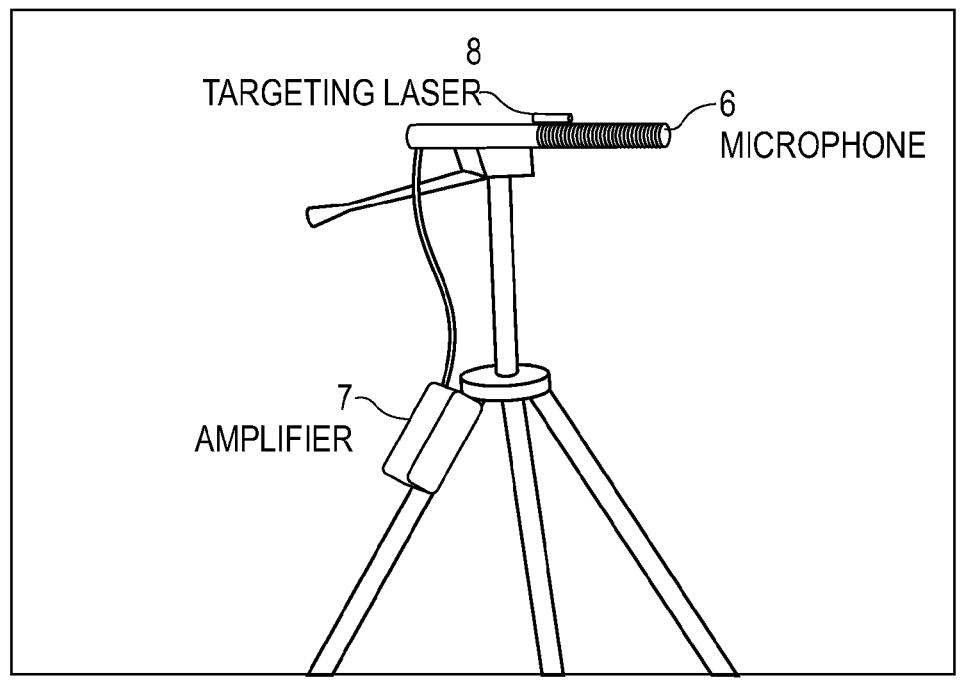
FIG. 3A depicts a tripod-mounted directional microphone with amplifier, as utilized in the Examples.
Figure 3B:
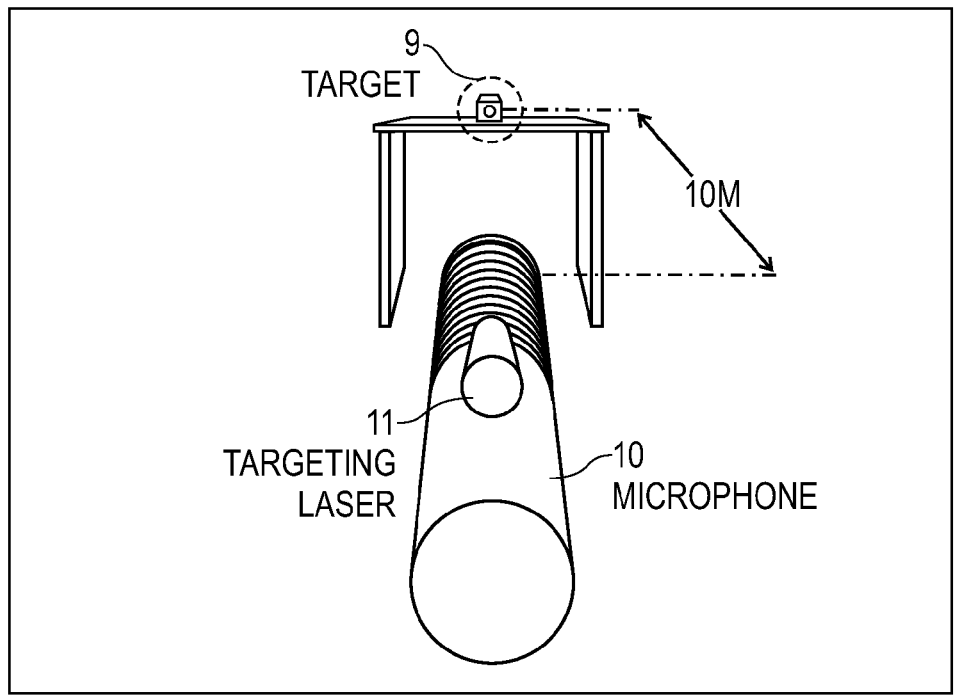
FIG. 3B depicts a view of a target from a microphone located 10 meters away, also as utilized in the Examples.

LIA signals were collected using a short condensing shotgun microphone located approximately 10 meters from the target area. The microphone was connected to an amplifier that, in turn, was connected to a 500 MHz A/D data acquisition board (Acqiris Model DP235, commercially available from Agilent Technologies, Inc., Santa Clara, Calif.). The DAQ board was triggered by the laser and used to record the audio signals. FIG. 3A shows the tripod-mounted directional microphone 6 with amplifier 7. FIG. 3B depicts a view of the target 9 from the microphone 10 located 10 meters away. The target is marked by the small, circled dot near the center of FIG. 3B. A small diode laser (the "Targeting Laser") 8 (FIG. 3A) or 11 (FIG. 3B) was used to point the microphone accurately at the target.

The LIA signal is a very short pulse, lasting approximately 0.1 ms, and appears as a spike in the background audio signal. (See, for example, FIG. 4.) This spike occurs approximately 30 ms after the initiation of the laser pulse at a microphone-to-sample spacing of 10 or 11 meters. The exact delay reflects the local speed of sound, which depends primarily upon the exact temperature in the laboratory and the exact distance between the microphone and target. In order to detect the LIA signal automatically, the sound spectrum was passed through a high-pass filter centered between 15 and 20 kHz. A conventional peak detection algorithm then was used to identify the LIA signals.

Figure 4:
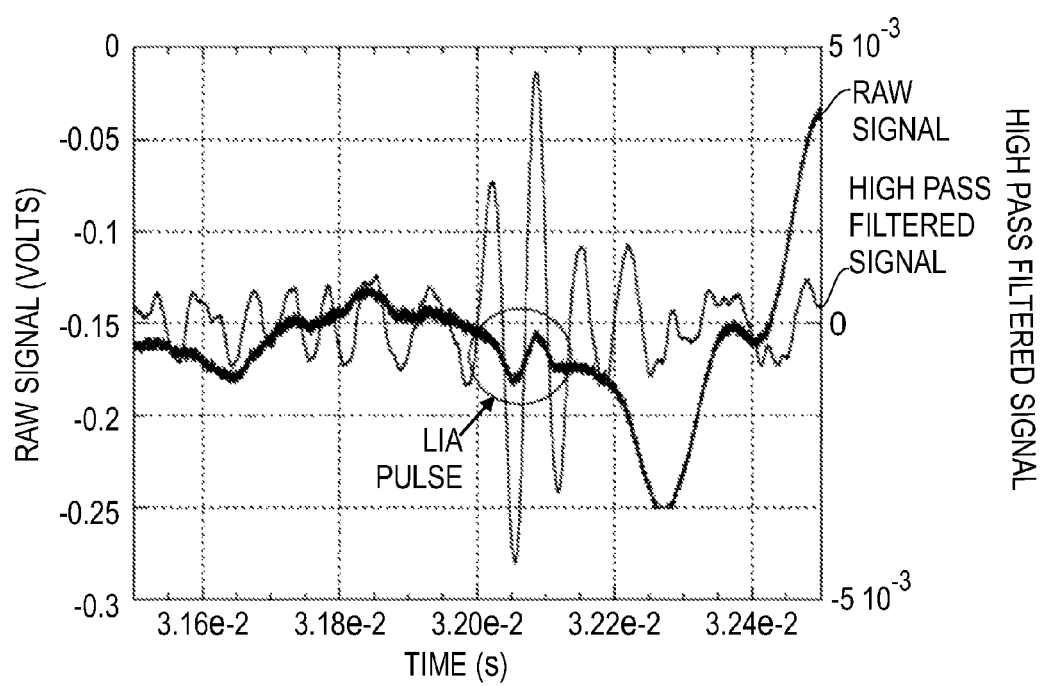
FIG. 4 is a graph showing a Raw Audio Signal (thick line) with High Pass Filtered Signal Overlaid (thin line).

FIG. 4 presents a graph demonstrating how a LIA pulse, collected by a microphone positioned 11 meters from the sample, is identified by a peak detection algorithm. A portion of the "raw" audio signal collected by the microphone is shown in FIG. 4 as the thick line. The LIA pulse's raw audio signal is circled in the middle of FIG. 4. The low amplitude of the raw LIA pulse normally makes it difficult to readily "pick out" from the background audio signal. Therefore, in order to be able to discern this small signal from an audio stream that may be 3 or 4 times longer than that showed in FIG. 4, it is important to take advantage of the fact that the LIA pulse is very short; that is, it is a high frequency signal or pulse. In fact, its frequency is approximately 20 kHz—higher than virtually all ambient noise. Therefore, processing the signal with a high pass filter dramatically brings out the pulse's presence. This is shown in the overlaid high pass filtered signal, shown in FIG. 4 as the thin line. The filtered signal has a very high amplitude only at the pulse's location, which allows the LIA pulse to be discerned much more easily. Using this approach, it is straightforward to identify LIA pulses against arbitrarily varying background noise from at least 11 meters away.

Example 1

LIA Measurements of Explosives in Silica Sand

LIA measurements were collected using explosives purchased from XM, a division of Van Aken International located near Los Angeles, Calif. (http://www.xm-materials.com/). The explosives consisted of either TNT (trinitrotoluene), RDX, or PETN deposited on silica particles. These coated particles typically are used for training dogs to detect explosives. TNT and RDX were present at 8% by weight in their respective samples, and PETN was present at 4% by weight. Uncoated silica particles also were used, in order to reduce the weight percentages of the explosives by dilution. Samples were prepared for analysis by spreading approximately 0.6 g of material on double-sided polyethylene tape, which was attached to the underside of a 37 mm diameter aluminum sample pan. Samples were irradiated at 266 nm from a CFR-400 laser (commercially available from Quantel USA, Bozeman, Mont.).

The LIA threshold of "explosive-free" silica on tape was determined by irradiating uncoated silica particles at gradually increasing laser pulse energies until a LIA signal was detected. This threshold was found to be 20 millijoules (mJ) per pulse, resulting in a surface energy density of 208 mJ/cm$^2$. In all subsequent tests on explosive-coated silica, a 10% lower pulse energy was used, and it was noted if a LIA signal was observed.

Figure 5:
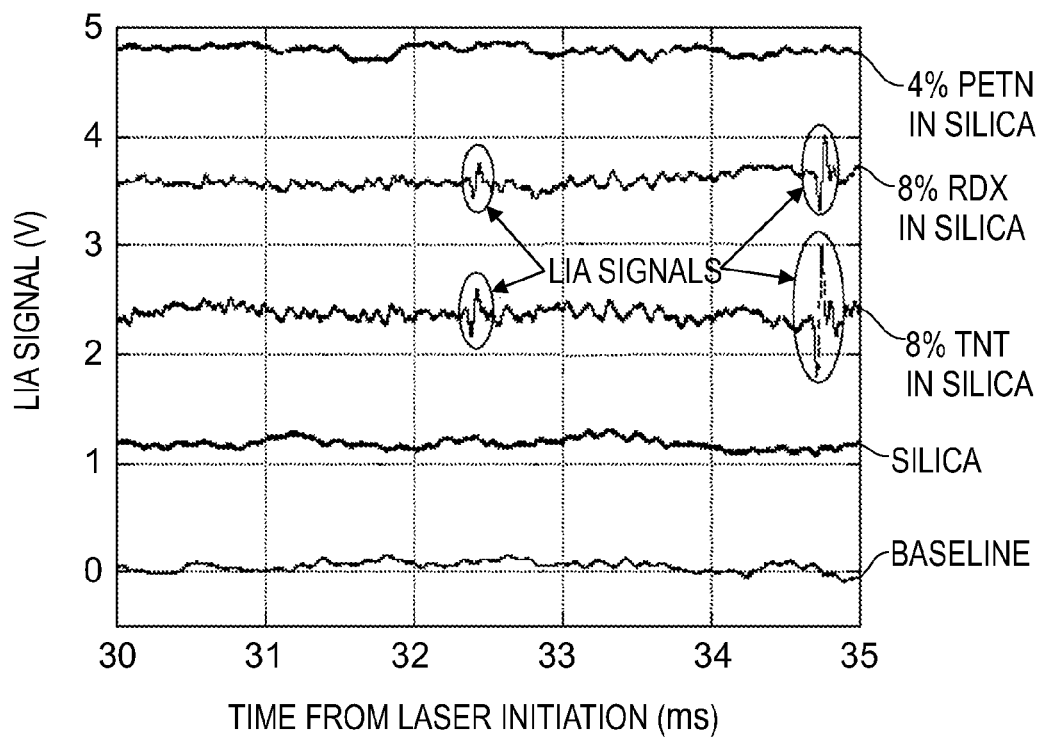
FIG. 5 is a graph showing "time-traces" of the changes in the LIA signals (measured in volts) generated by various explosive substances over time (measured in microseconds) from laser initiation. The respective substances are 4% PETN in silica, 8% RDX in silica, 8% TNT in silica, and uncoated (explosive-free) silica.

LIA tests on the 8% TNT and RDX coated silica samples exhibited a characteristic LIA disturbance 32.3 ms after the laser pulse (and an echo at 34.8 ms) as shown in FIG. 5. Each time-trace was collected from a single laser shot. The traces shown in FIG. 5 are separated by an offset of 1.2V to provide clarity. No LIA signal was detected for either the PETN coated silica or the uncoated silica samples. The "baseline" time-trace represents the signal (or lack thereof) from the substrate when there is no activation by the laser.

Figure 6A:
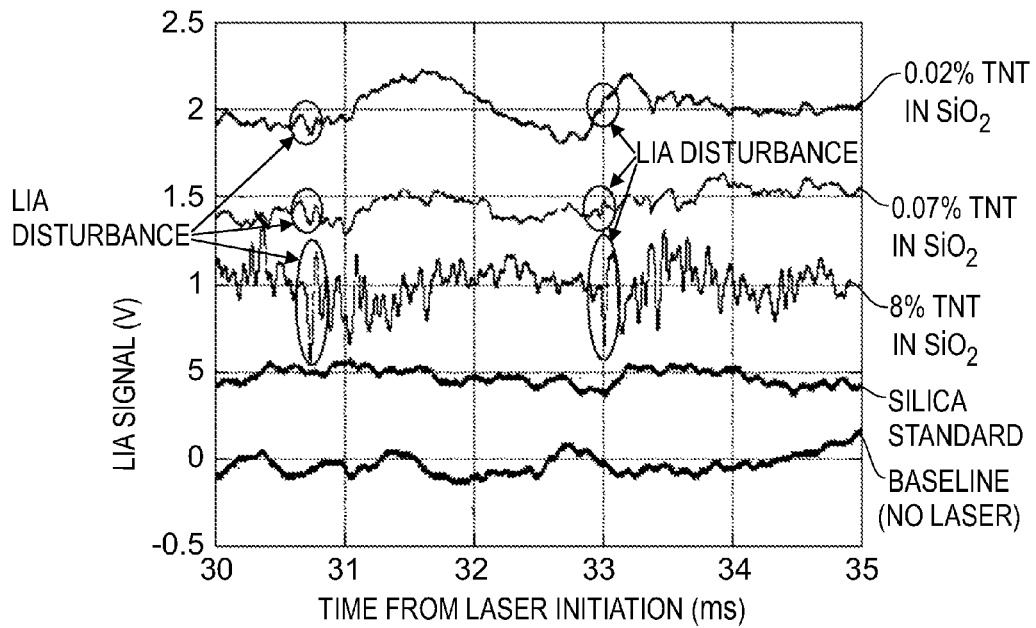
FIG. 6A is a graph showing LIA time-traces for various dilutions of TNT with silica.
Figure 6B:
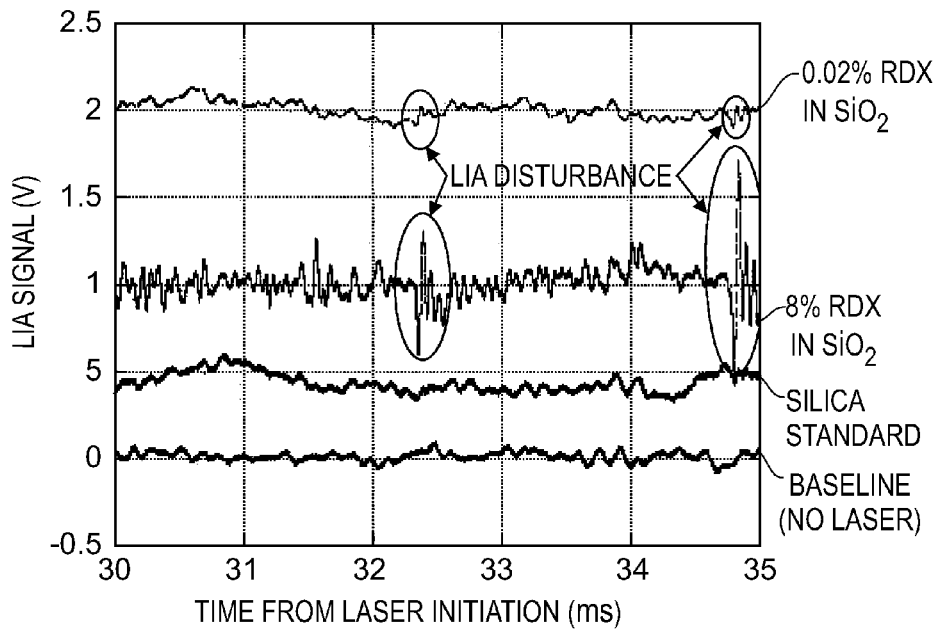
FIG. 6B is a similar graph for various dilutions of RDX with silica.

The limit of detection for TNT and RDX on silica particles was determined to be 10 μg/cm$^2$ (with the laser pulse energy kept constant). This limit of detection was determined by diluting the explosive coated particles with increasing amounts of uncoated particles until the LIA signals were indistinguishable from the silica standard. The results are illustrated in FIG. 6A for TNT and in FIG. 6B for RDX. Both TNT and RDX exhibited characteristic LIA disturbances, circled in FIGS. 6A and 6B, down to concentrations of 0.02% by weight, which corresponds to a surface loading of 10 μg/cm$^2$. These disturbances are not visible in the baseline and pure silica data.

Example 2

LIA Measurements of Non-Explosive in Silica Sand

Figure 7:
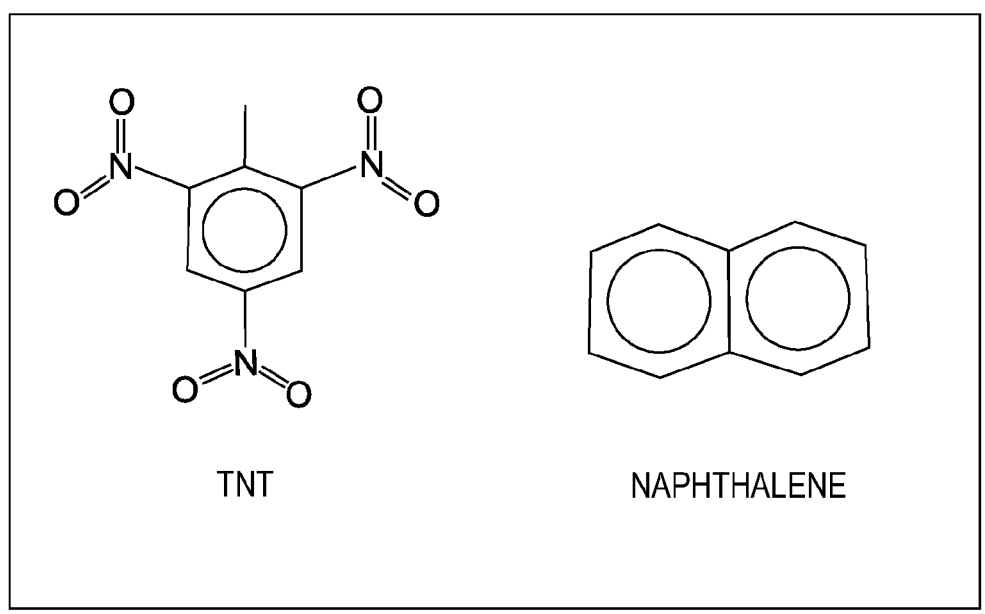
FIG. 7 depicts the chemical structures of TNT and naphthalene, respectively.

Further comparative experiments using naphthalene demonstrated that the LIA results presented in Example 1 may indeed be unique to explosives. Naphthalene is a non-explosive substance having a core molecular structure similar to that of TNT, as seen in FIG. 7. (The core structure of each molecule contains a benzene ring.)

To test the selectivity of LIA, experiments were conducted to see if adding naphthalene to silica produced LIA results different from that of TNT added to silica. A quantity of 99% pure naphthalene was ground and then mixed with silica sand to form an 8% naphthalene mixture for direct comparison with the 8% TNT coated silica sample tested in Example 1. LIA data were collected using the procedure of Example 1 on that sample and on additional mixtures with lower naphthalene concentrations, until a threshold was reached where the LIA disturbance was no longer detectable.

Figure 8:
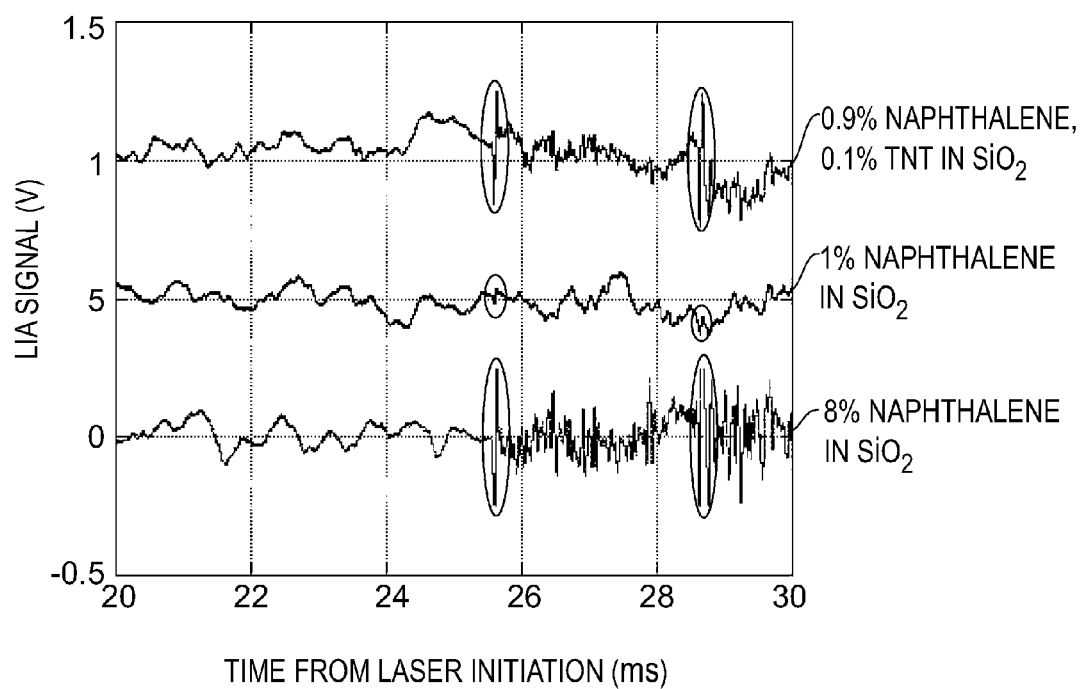
FIG. 8 is a graph, similar to those in FIGS. 5 and 6, showing LIA time-traces for various dilutions of naphthalene and/or TNT with silica.

Experiments on these samples demonstrated that the addition of TNT to a substance dramatically increases its reactivity with the laser pulses, even if that substance already is sensitive to the laser pulses. As shown in FIG. 8, the LIA signal for naphthalene at 8% exhibited a large spike around 25.7 ms after the laser fired and an echo at 29 ms. This is similar to the response of the TNT and RDX samples previously examined. The LIA signals were undetectable below a naphthalene concentration of around 1%, as also shown in FIG. 8. A small quantity of TNT was then added to the 1% naphthalene sample to form a mixture composed of 0.1% TNT, 0.9% naphthalene, and 99.0% SiO$_2$. As shown in FIG. 8, the addition of TNT resulted in a 500% increase in the amplitude of the LIA signal. Thus, while the LIA response may be partially related to molecular structure, there is evidence to suggest that there is another quality inherent in certain explosive materials such as TNT and RDX that dramatically enhances the effect, and that changes in the LIA intensity can be used to determine if a slight explosive residue is present on a material.

Example 3

LIA Measurements of Explosives in Petroleum Jelly

Subsequent experiments were performed to demonstrate that the LIA effect is not confined to explosive coatings on silica particles. Accordingly, LIA data were collected from small amounts of 8% TNT, 8% RDX, and 4% PETN in a petroleum jelly (i.e., Vaseline™) matrix, also acquired from XM. Samples were prepared by smearing a thin layer of material on the surface of a 37 mm diameter sample dish. As in the preceding Examples, the LIA measurements were taken at a distance of approximately 10 meters from each sample. The threshold laser energy for pure petroleum jelly was found to be slightly higher than 38 mJ/pulse, the maximum energy that the laser outputs at 266 nm. At this setting, the LIA effect on pure petroleum jelly was observed only intermittently. This may also have been due to the petroleum jelly thickness not being precisely uniform across the sample's surface. Based on this finding, the laser energy was set at its maximum value, and the experiment proceeded in order to identify any changes in the amplitude of the LIA signal in samples with explosive compounds.

Figure 9:
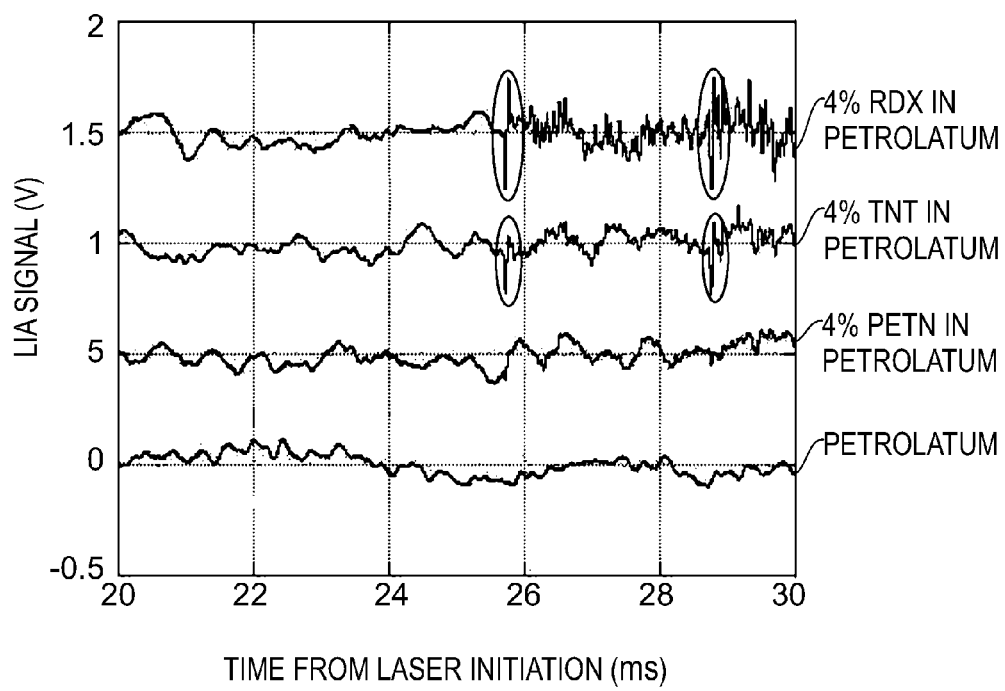
FIG. 9 is a graph, similar to those in FIGS. 5, 6 and 8, showing LIA time-traces, respectively, for 4% RDX in petrolatum, 4% TNT in petrolatum, 4% PETN in petrolatum, and explosive-free petrolatum.

It was found that much stronger LIA signals were observed for both the TNT and RDX samples as compared to the PETN and the pure petroleum jelly samples. This result in shown in FIG. 9, wherein the LIA time-traces are separated by an offset of 0.5V to provide clarity. The strong LIA response from TNT and RDX, and the corresponding weak response from PETN, therefore are common to both the silica and petroleum jelly substrates, even though the substrates' respective energy thresholds differed by a factor of two.

Example 4

LIA Measurements of Explosives with a 213 nm Wavelength Laser

A subsequent experiment was performed to test the effectiveness of LIA to detect the explosive PETN, using a nanosecond pulsed laser that emitted laser light pulses with a 213 nm wavelength. This wavelength is readily generated from the common Nd:YAG solid state laser design by quintupling the base laser frequency. The efficacy of this wavelength also was tested on the explosives TNT and RDX.

The rationale for this experiment was that the prior experiments, as described in Examples 1 and 3 above, had not successfully detected PETN using a 266 nm wavelength laser pulse, while RDX and TNT were readily detected. It was hypothesized that the 213 nm wavelength laser pulse could work for PETN because the solid phase absorption spectrum for PETN (i.e., the efficiency with which solid PETN absorbs light as a function of wavelength) has a peak near 200 nm, whereas the solid phase absorption spectra for TNT and RDX have maxima near 250 nm.

Equipment

The laser model emitted up to 3 mJ of energy in each pulse at 213 nm. This laser emits the 213 nm light together with the other harmonics of the laser (1064 nm, 532 nm, and 355 nm), but only the 213 nm light was directed towards the sample. The pulses were approximately 5 nanoseconds in length and approximately 3 mm in diameter.

The audio signals were captured approximately 15 inches away from the samples, using substantially the same equipment described in connection with Examples 1 through 3.

Samples

As in Example 1 above, the samples consisted of silica particles coated with either PETN (4% by weight), RDX (8% by weight), or TNT (8% by weight). For controls, uncoated silica particles were used, along with silica particles coated with evaporated sugar water (8%).

The other samples consisted of petrolatum (i.e., petroleum jelly or Vaseline™) as was used in Example 3 above, either pure or mixed with explosive compounds at the same weight percentages as for the silica particles.

Procedure

Experiments were performed at two different laser pulse energies: 1.7 mJ and 1.1 mJ. At the higher energies, the LIA signal from TNT exceeded the measurable range on the data acquisition card that was used to record the sounds.

25 signals were captured from each of the silica samples at 1.7 mJ; 5 signals, from each of the silica samples at 1.1 mJ; and 5 signals, from each of the petrolatum samples.

Figure 10:
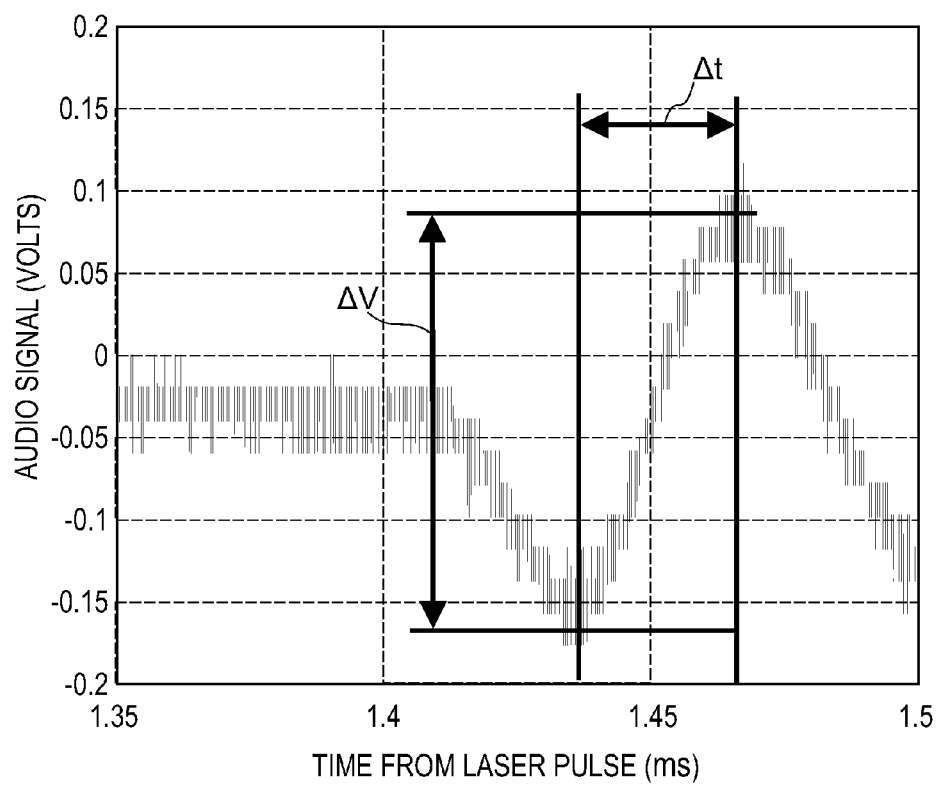
FIG. 10 is a graph showing the LIA signal from PETN at 1.7 mJ laser pulse energy. The graph demonstrates the temporal and voltage metrics that may be used to differentiate LIA signals from pure and contaminated samples.

Because a LIA pulse was detected from the pure silica and petrolatum at the 1.1 mJ energy level, it was determined that it would not be practicable to attempt to differentiate the various materials based on the mere presence or absence of a LIA pulse (since all materials—both with and without explosive contamination—would have been expected to produce a LIA pulse even at the laser's lowest energy level). Therefore, the goal of this experiment was to look for differences in the LIA signal between the pure and the contaminated samples as proof that LIA can detect explosives. In fact, it was found that the trough-to-peak voltage difference, and the temporal spacing between the trough and the peak, shown in FIG. 10 as $\Delta V$ and $\Delta t$, respectively, provided key information as to the effectiveness of LIA for explosives detection. In a preferred embodiment of the invention, as described in Example 6 below, a more mathematically robust analysis would be used for determining if a particular signal arose from an explosive compound. However the simple $\Delta V$ and $\Delta t$ analysis presented here serves to illustrate the concept clearly.

Results

The averages of measurements taken on all the samples is shown in Table 1, below. For the 1.1 mJ laser pulses on silica particles, both the $\Delta V$ and $\Delta t$ values are significantly lower for the pure silica particles and the particles coated with sugar. Combining the two measurements into an average slope of $\Delta V/\Delta t$, it can be seen in Table 1 that the explosive-laden samples have an average slope on the order of $10^{-3}$ V/µs, while the two inert samples have an average slope on the order of $10^{-4}$ V/µs.

The situation is very different for the case of 1.7 mJ laser pulses. In this case, the PETN $\Delta V$ is lower than that of both the other explosive samples and the inert samples. The $\Delta t$ values for all the samples are virtually identical. This results in the average slope being greatest for the TNT and RDX samples, moderate for the inert samples, and smallest for the PETN samples.

For the petrolatum samples, the $\Delta V$ measurements were very close for all the samples, while the $\Delta t$ values were nearly identical for the explosive samples and significantly shorter for the inert sample.

TABLE 1

Summary of LIA Temporal and Voltage Measurements

| Sample | Delta Volts | Delta Time | Average Slope |
|---|---|---|---|
| 1.1 mJ Laser Pulse on Silica | | | |
| SiO2 | 0.201 | 130.5 | 5.43E−04 |
| PETN | 0.446 | 295.2 | 1.56E−03 |
| RDX | 0.776 | 325.5 | 2.38E−03 |
| TNT | 1.341 | 326.0 | 4.14E−03 |
| Sugar | 0.179 | 76.0 | 2.09E−04 |
| 1.7 mJ Laser Pulse on Silica | | | |
| SiO2 180 | 0.702 | 325.0 | 2.17E−03 |
| PETN 180 | 0.313 | 318.9 | 9.80E−04 |
| RDX 180 | 3.289 | 328.6 | 1.00E−02 |
| TNT 180 | 4.721 | 319.8 | 1.49E−02 |
| Sugar 180 | 0.663 | 319.3 | 2.07E−03 |
| 1.7 mJ Laser Pulse on Silica | | | |
| Petrolatum | 0.250 | 258.5 | 6.05E−04 |
| PETN in Petrolatum | 0.260 | 364.9 | 7.17E−04 |
| RDX in Petrolatum | 0.331 | 360.5 | 9.19E−04 |
| TNT in Petrolatum | 0.314 | 378.5 | 8.31E−04 |

Conclusions

There appears to be a threshold energy for the silica samples below which the PETN samples generate a signal that resembles that of TNT and RDX, allowing it to be readily detected. At 1.7 mJ pulse energy, this difference disappears and to some extent reverses. While this reversal may also potentially be used to detect PETN, the fact that this energy does not group PETN with the other explosive compounds makes this likelihood small.

For the case of the petrolatum samples, the difference between the inert and explosive samples manifests itself mostly in the duration of the LIA pulse as measured by $\Delta t$. The $\Delta V$ measurements did not exhibit nearly the same range as for the silica particles, and the PETN and pure petrolatum samples had essentially identical $\Delta V$ averages. However, the $\Delta t$ value for the PETN sample clearly falls into the TNT and RDX group.

It therefore was concluded that PETN can be detected via LIA with a 213 nm wavelength laser, provided that the laser pulse energy is below the applicable threshold energy for the silica particles. This detection can be performed using measurements of the average slope of the LIA waveform. For the case of petrolatum samples, the average duration of the LIA pulse provides the best means of detecting the presence of TNT, RDX, or PETN.

Practical Considerations

Implementing LIA for explosives detection using a 213 nm wavelength laser appears to require having some knowledge of the material being interrogated. This knowledge can be acquired in practice using at least two other laser-based stand-off material analysis methods, such as LIBS and Raman Spectroscopy. As stated previously, an especially preferred embodiment of the present invention comprises a single sensor apparatus that combines LIA, LIBS and Raman Spectroscopy functionalities. With the information that these methods can provide, the material being interrogated by LIA can be identified, allowing for the proper laser threshold energy to be used to detect whether explosives are present.

Example 5

LIA Measurement of Non-Nitrogen-Based Explosive

In a follow-up experiment, it was established that LIA also can be used to detect TATP (triacetone triperoxide), the explosive brought onto an airplane by the would-be "Shoe Bomber" to detonate the main charge of PETN, and probably also used in the subsequent London subway bombings. This is a significant development, because TATP is not in the same family of explosives as TNT, RDX, and PETN. TATP is a peroxide-based explosive, whereas the others all are nitrogen-based. Prior art explosive detection technologies that look only for nitrogenous explosives would be ineffective with TATP.

Limited experiments with TATP demonstrated that LIA is a highly sensitive method for detecting this explosive, with sensitivity down to the single $\mu g/cm^2$_range. The experiments were conducted following the same general procedures and using the same 266 nm laser described above in connection with Example 1. The samples were silica particles coated with TATP solution and dried. The surface loading of TATP was 6.4 $\mu g/cm^2$, and the laser beam diameter was approximately 1 cm. The resulting LIA signals were compared with those produced by (a) plain silica particles and (b) particles coated with a table sugar solution and dried. The loading of the sugar was 8% by weight. Each sample was shot 25 times, and the results were averaged. The results are summarized in Table 2.

TABLE 2

Summary of LIA Results on TATP

| Sample | Delta Volts | Delta Time | Average Slope |
| --- | --- | --- | --- |
| SiO2 | 0.999 | 322.7 | 3.12E−03 |
| Sugar | 0.395 | 328.7 | 1.26E−03 |
| TATP | 1.942 | 321.8 | 6.03E−03 |

As can be seen from Table 2, adding a small amount of TATP dramatically increases the amplitude of the LIA signal from the particles, as measured by $\Delta V$. This suggests that LIA can be effective in detecting peroxide-based explosives in the field with high sensitivity.

Example 6

Selection and Use of Chemometric Methods

Applying chemometric methods to different signals, whether acoustic or electromagnetic, to identify a substance under study has been proven to be effective in a wide range of fields. A book describing chemometrics in general, including the methods known as Principal Components Analysis and Regression (i.e. PCA/PCR), and Partial Least Squares Analysis and Regression (i.e. PLS, PLSDA, PLSR), is Naes, Tormod, Isaksson, Tomas, Fearn, Tom, and Davies, Tony, *Multivariate Calibration and Classification*, NIR Publications, West Sussex, UK, 2002. A useful review of chemometric methods applied to the field of spectroscopy can be found in Geladi, Paul, "Chemometrics in spectroscopy. Part 1. Classical chemometrics", Spectrochimica Acta Part B, 58, 2003, pp. 767-782. In the area of acoustic signals, the chemometric method Gaussian Mixture Models (i.e. GMM) was combined with the machine learning method Support Vector Machines (i.e. SVM) to analyze different sounds made by whales and dolphins as described in Roch, Marie A., Soldevilla, Melissa S., Hoenigman, Phonda, Wiggins, Sean M., and Hildebrand John A., "Comparison of Machine Learning Techniques for the Classification of Echolocation Clicks from Three Species of Odontocetes," Canadian Acoustics, 36, No. 1, 2008, pp. 41-47.

Tree Bagging, also known as Random Forest, is a machine learning technique that has also been applied to identifying the sources of acoustic signals. The technique was first described by Breiman, Leo, "Random Forests", Machine Learning, 45, No. 1, 2001, pp. 5-32. It was used to classify the cries of babies by Amaro-Camargo, Erika and Reyes-Garcia, Carlos A., "Applying Statistical Vectors of Acoustic Characteristics for the Automatic Classification of Infant Cry", ICIC'07 Proceedings of the Intelligent Computing $3^{rd}$ International Conference on Advanced Intelligent Computing Theories and Applications, Huang, D, Huette, L., Loog, M. Eds., Springer-Verlag, Heidelberg, 2007, pp. 1078-1085. It also was used to classify bat echolocation calls by Armitage, David W. and Ober, Holly K., "A Comparison of Supervised Learning Techniques in the Classification of Bat Echolocation Calls," Ecological Informatics, 5, Issue 6, November 2010, pp 465-473.

An example of how chemometrics and machine learning are used with LIA data to identify an explosive residue will illustrate the principles involved. LIA signals were collected from six different explosives: TNT, C4, HMX, PETN, ANFO and urea nitrate (UN). In addition, LIA signals were collected from nine clean surfaces: aluminum, cardboard, chrome plated steel, double sided adhesive tape, glass, nylon cloth, automotive paint, zinc plated steel, and gift wrapping paper. As described in the following paragraphs and in FIG. 11, seven different, well-known classifiers were investigated: (1) Ada Boost, (2) Generalized Likelihood Ratio Test ("GLRT"), (3) K Nearest Neighbor ("Knn"), (4) Support Vector Machine ("SVM"), (5) Naive Bayes, (6) Partial Least Squares Discriminant Analysis ("PLSDA"), and (7) Tree Bagging.

Figure 11:
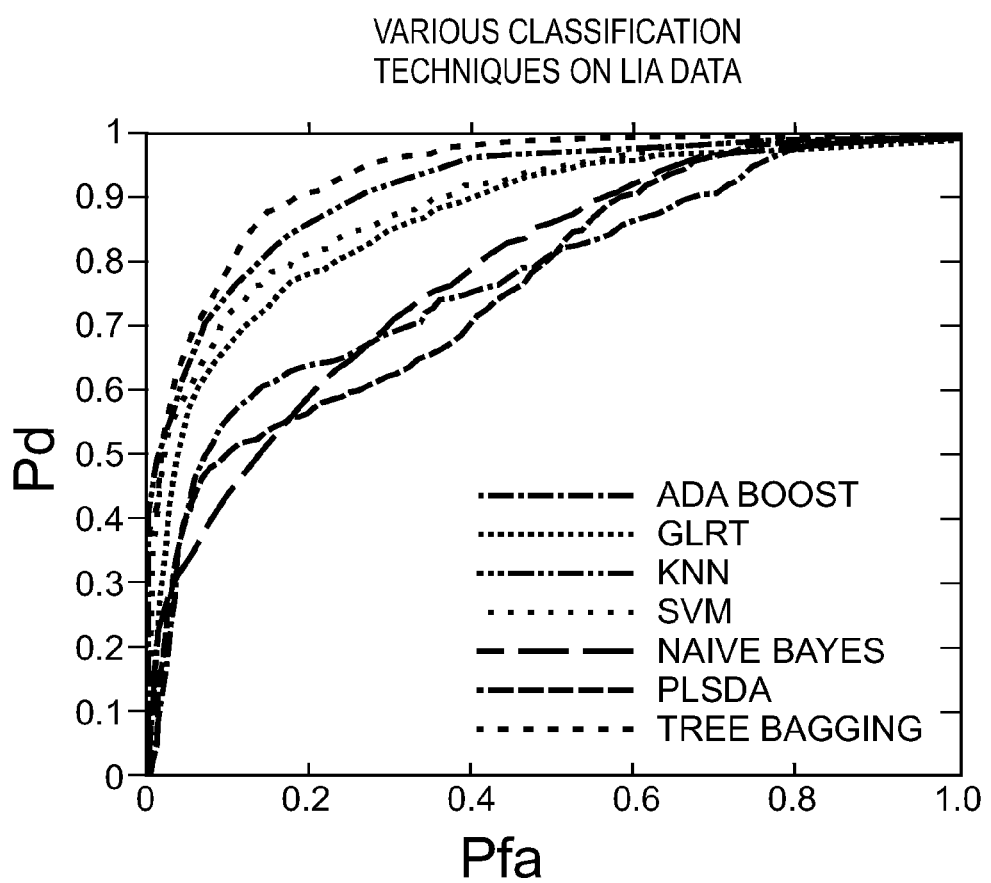
FIG. 11 is a graph comparing the Receiver Operating Characteristic (ROC) curve for seven different potential classifier algorithms.

Approximately 80% of the LIA signals were used to train the various classifiers. All the signals were classified as belonging to either the explosive group or the inert material group. The remaining 20% of the signals were then used to test the classifiers. The output of the classifier is a number between 0 and 100%, indicating the level of certainty that the signal being analyzed is from an explosive. By choosing a threshold, say 75%, the practitioner can count how many signals were classified correctly. By varying this threshold from 0 to 100%, the practitioner can trace out what is known as the Receiver Operating Characteristic (ROC) curve, which plots the number of correctly classified LIA signals from explosives, (i.e., probability of detection or Pd) as a function of the number of incorrectly classified LIA signals from inert substances (i.e., probability of false alarms or Pfa). The ROC curve for this test for the various classifier algorithms is shown in FIG. 11. Tree Bagging was the best performing algorithm, since it had the highest Pd value for any given Pfa value.

It should be noted that the performance shown here should not be understood as being the optimal or typical performance achievable in every case with LIA technology. It is merely an example.

Other possible implementations of chemometric methods include devising a separate classifier for each explosive or each type of explosive (e.g., nitrogenous, peroxide, etc.). Similarly, rather than group all inert substances together, different classifiers can be constructed for different inert substances or classes of inert substances (e.g., metals, plastics, etc.). In addition, a classifier can be constructed using only explosive LIA signals and no signals from inert substances. In this case, the algorithm flags LIA signals that are good matches for the ones in the training library as arising from an explosive material.

The results shown in FIG. 11 would be implemented in a LIA sensor in the following way: The desired operating point on the ROC curve would be chosen according to the scenario where the device would be used. For example, if it is decided that a 90% probability of detection is required and the 20% false alarm rate can be tolerated, then the threshold value corresponding to that point on the ROC curve is selected. Whenever a new LIA signal is collected, it is processed by the classification algorithm. If the resulting score is above the threshold then the response is reported as being from an explosive compound. If the classification confidence is beneath the threshold, no alert is given.

When scanning a surface, it may be advantageous to only alert the sensor operator if more than one explosive LIA signal was detected within a certain sized area. Requiring this confirming information would prevent excessive false alarms from being reported.

Example 7

Portable Sensor Devices

Figure 12:
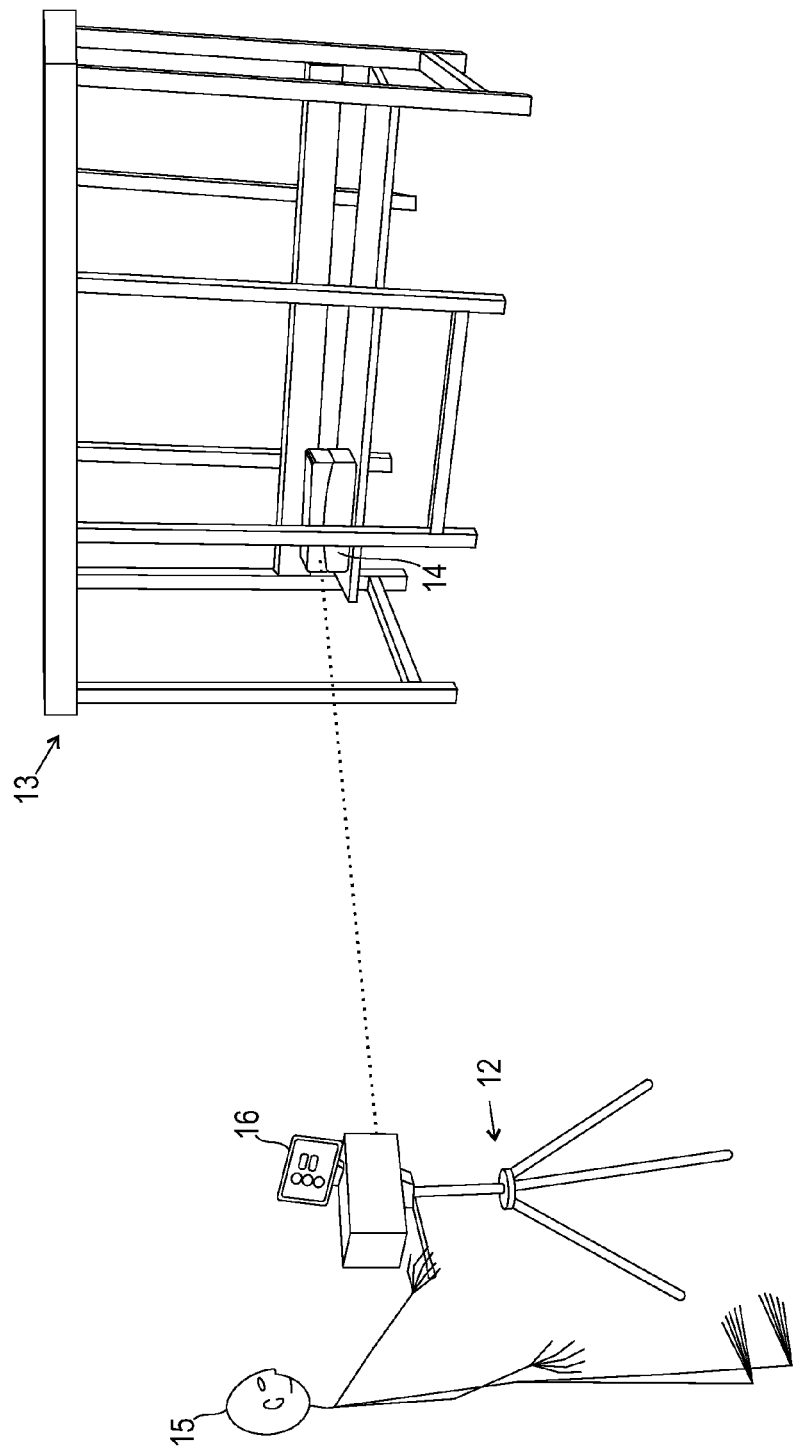
FIG. 12 is a pictorial representation of an embodiment of a portable LIA sensor, deployed at a public bus stop to test an abandoned bag for the presence of explosives.

FIG. 12 depicts one possible embodiment of LIA technology into a sensor device. LIA technology is deployed in FIG. 12 as a battery-powered portable scanner 12 brought to a bus stop 13 after an alert from an observant passerby to an abandoned bag 14. The first responder 15 scans the surfaces of the bag 14 with the LIA sensor to determine if explosive residue is present. The sensor 12 immediately reports the result of the scan on the included monitor 16 on the top surface of the sensor 12. Since the sensor 12 is battery-powered, there is no need for finding an electrical outlet or bringing a portable generator, increasing the number of scenarios and locations where the sensor 12 can be used. The sensor 12 is also ruggedized for indoor and outdoor operation. For example, the screen 16 is chosen to be one that is readable in sunlight, and the entire sensor 12 is water resistant for operation in rainy conditions. The display 16 uses a "red-yellow-green" scheme where a red signal indicates that an explosive residue has been found, a green signal indicates that no explosive residue was found, and yellow indicates an inconclusive reading. Optionally, if an explosive residue is found, the system may also report the most likely explosive(s) or type of explosive(s) that was found.

Although FIG. 12 shows a system wherein a microphone is used for collecting the LIA signal, other technologies may be more suitable for a particular application, especially if longer standoff distances are involved than what is shown in FIG. 12. One such technology is Laser Doppler Vibrometry (LDV), which measures the vibration of a surface with a laser as a proxy for the acoustic signal. The benefits of using an LDV device over a microphone are immunity from ambient noise, the ability to measure very high frequencies that are difficult to measure using a microphone because they are attenuated by ambient air, and the capability for longer standoff measurements without the use of a large sound concentrator like a parabolic dish.

Another option that may be more suitable for longer standoff distances is replacing the single microphone in FIG. 12 with an array of microphones. An array of microphones can act, when used with suitable signal processing software, such as Pulse software from Bruel & Kjaer (Denmark), as a directional microphone with enhanced sensitivity and noise rejection. This is also known as beamforming. The benefits of using an array of microphones over a single microphone with a sound concentrator are that the array does not need to be precisely pointed at the sound source, the array can be more discreet than the concentrator, and the array does not distort the sound as a concentrator inevitably does because sound reaches the single microphone at the focal point of the concentrator from multiple paths (i.e., from the edge of the concentrator as well as from locations closer to the center of the concentrator). By contrast, in an array of microphones each microphone receives an undistorted signal.

EYE SAFETY

Laser based detectors must be eye safe, or nearly so, if they are to be broadly deployed. U.S. laser system manufacturers use the maximum safe exposure levels published by the American National Standards Institute Inc. (ANSI) for all types of lasers. (*American National Standard for Safe Use of Lasers*, ANSI Z136.1-2007, The Laser Institute of America, Mar. 16, 2007.) The ANSI designations are termed Class 1 through Class 4, with Class 1 being completely safe even without laser safety glasses or training, and Class 4 being the most dangerous to the eye and skin. Class 1 laser systems are not necessarily those with the lowest laser power. Systems using Class 4 lasers, when properly interlocked, can receive a Class 1 designation.

By using a deep UV laser for LIA measurements in accordance with the present invention, the problem of laser safety immediately becomes more tractable. In fact, deep UV lasers have permissible energy density thresholds 1000 to 6000 times higher than those of longer wavelength lasers. According to the ANSI standard, the ocular maximum permissible exposure (MPE) for a nanosecond class pulsed laser operating at deep UV wavelengths (180 nm$\leq\lambda<$302 nm) is 3000 $\mu J/cm^2$ for a single pulse. This is in contrast to visible wavelengths (400 nm$\leq\lambda<$700 nm), where the MPE is 0.5 $\mu J/cm^2$, 6000 times lower than the deep UV value. For near IR lasers (700 nm$\leq\lambda<$1050 nm), which are often used in Raman Spectroscopy, the MPE value is between 0.5 $\mu J/cm^2$ and 2.5 $\mu J/cm^2$ depending on wavelength. Even the top of this range is still more than 1000 times smaller than the deep UV limit.

Using a deep UV laser also has benefits with regard to concerns over reflected beams, since most materials absorb deep UV radiation very well and reflect it very poorly. In fact, ordinary glass, whether in a building's window pane, an automobile window, or a pair of reading glasses will completely block deep UV radiation, as do clear plastics. Virtually all opaque surfaces, including polished metal surfaces, will reflect less than half of incident deep UV radiation. Focusing the laser pulses onto the suspect surface also ensures that any reflected light rapidly disperses with increased distance from the sample.

The central issue, therefore, is protecting people from the direct beam by using safety interlocks, and ensuring that no one is standing in the relatively small area where the reflected beam can be dangerous. In fact, the reflections from diffuse surfaces (i.e. surfaces without mirror finishes) are not a concern at all if the laser can be engineered to be Class 3b or lower. Therefore, the most important objective is to protect people from the direct laser beam. This objective is achieved in accordance with a further aspect of the invention.

Figure 13:
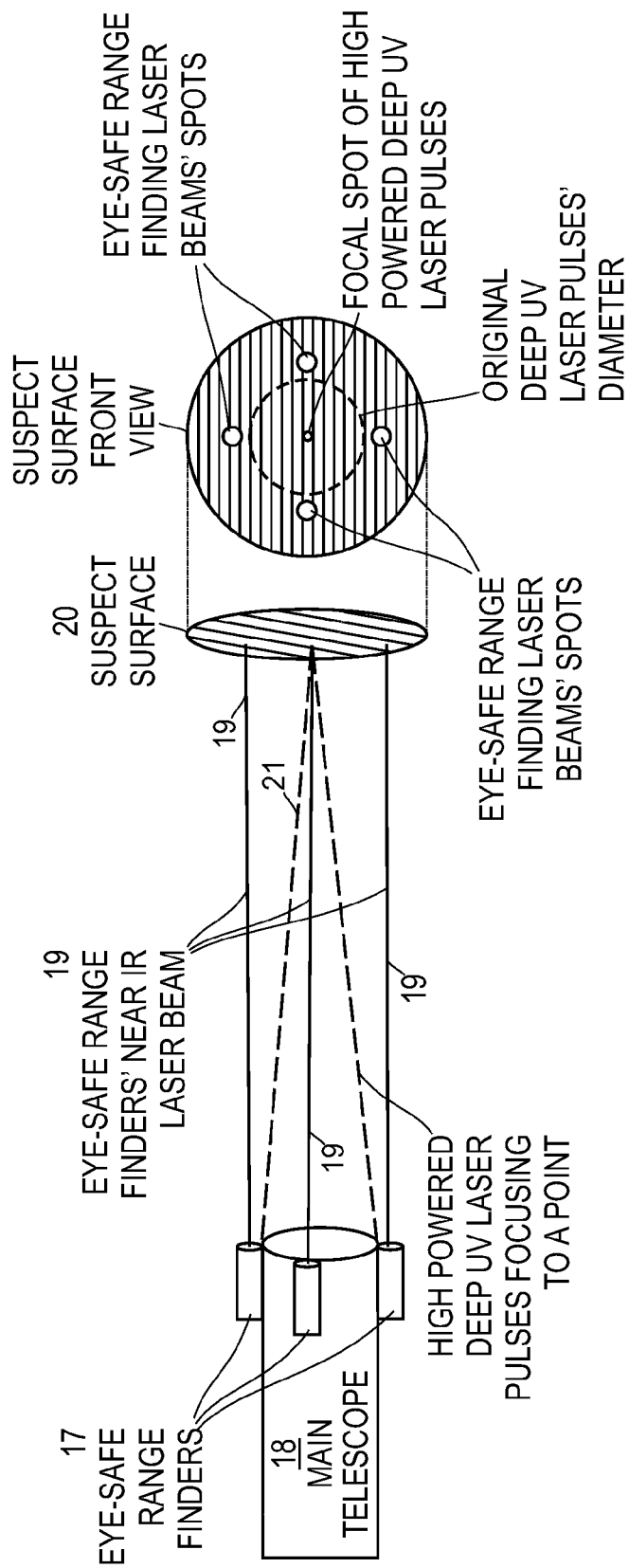
FIG. 13 is a schematic drawing of a scheme for eye-safe operation of a stand-off explosive detector, in accordance with the invention.

The present invention advantageously uses Class 1 or 2 visible wavelength or near IR range-finding lasers as optical "trip wires." This is done by aiming several of these beams at locations on the suspect surface, but off-center from the primary UV laser's ("telescope's") focal spot, as is shown schematically in FIG. 13.

As depicted in FIG. 13, four ancillary, range-finding lasers 17 are positioned circumferentially about the primary UV laser 18, so that their respective beams 19 (the term "laser beam" should be understood also to refer to a stream of laser pulses) strike the surface of interest 20 outside the area irradiated by the primary laser beam 21. (It will, of course, be understood that more or fewer than four range-finding lasers can be used in accordance with the invention.) The range-finding ancillary lasers 17 operate continuously, while the telescope 18 is firing discrete UV laser pulses 21 at the surface. Should a person approach the focal spot of the telescope, one of the ancillary beams 19 would be broken, which would register as sudden reduction in the computed range to the target 20. This serves as a signal to the system (i.e., an "interlock") to immediately shut off the UV laser 18.

Other safety interlocks encompassed by the invention may include limiting the range to target over which the UV laser will fire. In this way, it will not fire by accident at very near targets such as the operator or other nearby personnel, or very far away targets such as aircraft. Since the laser pulse duration is on the order of nanoseconds, while the time between pulses is typically at least ten milliseconds, there is ample time to switch off the laser should a person come close to the focal spot of the telescope.

It should be noted that the inventive eye-safety method also can be used for other applications involving free space laser beams or pulses, such as Laser Induced Breakdown Spectroscopy (LIBS), Raman Spectroscopy, and laser-based entertainment displays. It can also be used for preventing excess exposures from laser wavelengths other than the deep UV.

A further novel method for protecting eyes from laser light, in accordance with the invention, involves exploiting the fact that exposure times used to calculate permissible ocular exposures for visible lasers are very low, so that placing a visible laser beam coincident with the primary, invisible deep UV laser 21 (as shown in FIG. 13) can result in a much safer laser system. Laser pointers and other visible wavelength lasers of similar power ranges can be legally used in public without laser safety glasses because a human reflexively turns away from the beam should it shine into an eye. ANSI considers this reflex as a means of limiting exposures to continuous wave (as opposed to pulsed) visible lasers to 0.25 seconds. Therefore, if such a visible beam is coincident with the UV laser pulses, then the maximum ocular exposure to the UV beam is 0.25 seconds worth of pulses. Typical lasers used for LIA will run between 5 Hz and 100 Hz, so the maximum exposure would be for a total of 1 to 25 pulses. Without this safety feature, the laser would likely run for a burst of 10 seconds or longer to make a measurement, and so the laser safety calculations would have to consider the much more dangerous exposure of a minimum of 50 to 1000 pulses. Therefore, this additional eye-safety method, involving the use of visible laser beams, has the effect of reducing potential human exposure to UV laser beams by a factor of 40 to 50.

The foregoing description details certain embodiments of the invention. It will be appreciated, however, that the invention can be practiced in many ways. It also should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method for improving the eye-safety of potentially harmful, primary laser pulses, comprising the steps of:
    (a)(i) positioning one or more ancillary lasers, so that an ancillary laser beam or stream of laser pulses is proximate to, but at least partially outside, an area irradiated by the primary laser pulses; and/or
    (ii) disposing a visible laser beam so as to be substantially coincident with said primary laser pulses; and
    (b) in the event of any discontinuity in said ancillary laser beam or stream of laser pulses, generating a signal to shut off the primary laser.

2. The method of claim 1, wherein said ancillary laser comprises a visible wavelength or near IR range-finding laser.

3. The method of claim 1, further comprising limiting the range to target over which the primary laser will fire.

4. An apparatus for improving the eye-safety of potentially harmful, primary laser pulses, comprising:
    (a)(i) means for positioning one or more ancillary lasers, so that an ancillary laser beam or stream of laser pulses is proximate to, but at least partially outside, an area irradiated by the primary laser pulses; and/or
    (ii) means for generating a visible laser beam disposed so as to be substantially coincident with said primary laser pulses; and
    (b) means for generating a signal to shut off the primary laser in the event of any discontinuity said ancillary laser beam or stream of laser pulses.

5. The apparatus of claim 4, wherein said ancillary laser comprises a visible wavelength or near IR range-finding laser.

6. The apparatus of claim 4, further comprising means for limiting the range to target over which the primary laser will fire.

* * * * *